United States Patent [19]
Warters

[11] Patent Number: 5,605,149
[45] Date of Patent: Feb. 25, 1997

[54] METHOD AND APPARATUS FOR DIRECTING AIR FLOW WITHIN AN INTUBATED PATIENT

[75] Inventor: Robert D. Warters, Houston, Tex.

[73] Assignee: Board of Regents, The University of Texas System, Austin, Tex.

[21] Appl. No.: 406,310

[22] Filed: Mar. 17, 1995

[51] Int. Cl.$^6$ ................................................. A61M 16/00
[52] U.S. Cl. .................. 128/207.14; 128/207.15; 128/207.16; 128/209.18; 128/205.27
[58] Field of Search .................. 128/207.14, 207.15, 128/207.16, 204.18, 205.19, 205.27, 200.26; 604/54, 94, 173, 264, 280–284

[56] References Cited

U.S. PATENT DOCUMENTS

| | | | |
|---|---|---|---|
| 3,754,554 | 8/1973 | Felbarg | 128/207.14 X |
| 3,788,326 | 1/1974 | Jacobs | 128/207.15 |
| 3,844,290 | 10/1974 | Birch et al. | 128/351 |
| 4,026,296 | 5/1977 | Stoy et al. | 128/207.15 X |
| 4,327,720 | 5/1982 | Bronson et al. | 128/207.15 |
| 4,416,273 | 11/1983 | Grimes | 128/207.16 |
| 4,538,607 | 9/1985 | Saul | 128/207.16 |
| 4,595,005 | 6/1986 | Jinotti | 128/205.24 |
| 4,646,733 | 3/1987 | Stroh et al. | 128/207.16 |
| 4,773,412 | 9/1988 | Blom | 128/207.14 |
| 4,840,173 | 6/1989 | Porter, III | 128/207.15 |
| 5,143,062 | 9/1992 | Peckham | 128/207.14 |

FOREIGN PATENT DOCUMENTS

| | | | |
|---|---|---|---|
| 1516118 | 10/1989 | U.S.S.R. | 128/207.14 |

Primary Examiner—Aaron J. Lewis
Assistant Examiner—Eric P. Raciti
Attorney, Agent, or Firm—Arnold, White & Durkee

[57] ABSTRACT

A novel method and apparatus for directing air flow and for removing internal secretions within an intubated patient is disclosed. In one respect, the invention contemplates an air flow assembly including a conduit coupling assembly coupled to an expansible conduit. The conduit coupling assembly includes a housing with an upper flow connector and a lower flow connector; a recess at its lower end; and an annular, valved partition defining an annular chamber within the housing below the partition. The lower flow connector is configured to be connected to the upper or proximal end of an endotracheal tube so as to form an annular passageway between the endotracheal tube and the expansible conduit. The upper flow connector is adapted to receive air or other desired gas from a suitable source. The partition includes a one-way flow valve or other device for enabling flow of gas selectively through the housing. The method disclosed includes the steps of intubating a patient with a first conduit; supporting an expansible conduit within the first conduit to define an annular passageway; circulating gas down the expansible conduit and up the annular passageway, and separating liquid from circulated gas at the upper end of the annular passageway. In another respect, an apparatus is disclosed having a air conduit with an internal partition defining an inspiratory air pathway and a separate expiratory air pathway, so that with each exhalation secretions are forced progressively out through the separate expiratory air pathway. A corresponding method to this alternative apparatus is also disclosed.

20 Claims, 4 Drawing Sheets

5,605,149

METHOD AND APPARATUS FOR DIRECTING AIR FLOW WITHIN AN INTUBATED PATIENT

BACKGROUND OF THE INVENTION

1. Field of Invention

The present invention relates to ventilation of a hospital patient through an endotracheal tube inserted into the trachea of a patient. More particularly, the present invention relates to a flow system that provides for continuous removal of secretions from within an intubated patient.

2. Prior Art

Intubation involves the insertion of a conduit into the trachea of a patient. One of the most commonly used conduits is an endotracheal tube. For intubation, the distal end of the endotracheal tube is extended into the trachea of a patient. The endotracheal tube generally terminates in a patient at a position above the carina and interior to a position between the second and fourth thoracic vertebrae. Gasses may then be introduced into the lungs of the patient through the endotracheal tube.

Purposes for intubation include providing mechanical ventilation of a patient's lungs (e.g., when a disease prevents the patient from normal breathing-induced ventilation), and providing a conduit for anesthetic gasses during a surgical procedure. To prevent the escape of gasses past the endotracheal tube once inside of an intubated patient, an inflatable cuff may be included at the distal end of the endotracheal tube. When inflated, the cuff seals the annular passageway between the endotracheal tube and the tracheal wall. This inflatable cuff may be formed integral with and surrounding the endotracheal tube. There are approximately 17,000 patients in critical care units in the United States on any given day, of which approximately 60% may require intubation. Although intubation is often a life-saving maneuver, intubation unfortunately tends to create serious adverse effects on a patient's ability to clear secretions and particles from their lungs.

In a non-intubated person, inhaled particulate matter is normally cleared from the lungs by a patient's natural mucociliary transport system. The natural mucociliary transport system is composed of cells, which line the tracheobronchial tree and which have cilia (tiny hairs) on their surfaces. The cilia sweep particles up so that coughing can expel the particles from the body. These cells also produce mucous that provide a fluid phase to facilitate transport. Secretions from the tracheobronchial tree are also normally removed through the constant motion of the tiny cilia which line the trachea.

In an intubated patient, however, the endotracheal tube tends to impair the functioning of the natural mucociliary transport system. Initiation of a cough requires glottic closure in order to generate the intrathoracic pressure required to effectively expel material from the trachea. The presence of the endotracheal tube prevents an intubated patients from closing their glottis. Further, ciliary function and mucociliary transport in the trachea, which may be impaired by infection such as pneumonia or tracheobronchitis, is also impaired by the endotracheal tube, which tends to block the upward movement of secretions. Thus, it is common for intubated patients to have internal secretions pool in the patient's lungs distal to the sealing cuff on an endotracheal tube.

Accumulation of fluids, particulate matter, and internal secretions in the lungs of intubated patients give rise to critical problems and infections in these patients, such as atelectasis and pneumonia. The risk of such infection and other problems generally increase with increased length of time of intubation. It is well-documented that a relatively high mortality rate is associated with prolonged intubation. Removal of pooled secretions from intubated patients is, therefore, an integral part of the care of such patients.

The standard technique for removing internal secretions from an intubated patient is to suction pooled secretions directly from the lungs of the patient. This standard technique, however, has significant disadvantages. For example, direct suctioning requires the periodic efforts of a trained health care professional and often occurs on an intermittent basis of about once every one to two hours, due to labor and time constraints. Secretions within the lungs of an intubated patient, therefore, may accumulate and pool for significant time periods. Further, every time the ventilator system is exposed to allow direct suctioning of pooled secretions from an intubated patient, the risk for contamination and subsequent infection tends to increase. Direct suctioning has been associated with severe complications including hypoxemia, cardiac arrhythmias, decreased oxygen delivery, cardiac arrest, mucosal trauma, and raised intracranial pressure.

The standard technique for removing secretions from an intubated patient is, therefore, inherently inefficient and risks contamination of the patient. The goal of the present invention is to provide an apparatus and technique for directing air flow within an endotracheal tube and for removing secretions from an intubated patient, while overcoming problems associated with prior devices and techniques.

SUMMARY OF THE INVENTION

The present invention addresses the problems discussed above by providing a system that directs air flow within an endotracheal tube, enables a continuous removal of secretions from an intubated patient, and reduces or eliminates the need for direct suctioning.

In one general respect, the present invention contemplates an air flow assembly positionable within a patient including an air conduit positionable within a patient having an inspiratory pathway and a separate expiratory pathway; and a conduit coupling assembly coupled to the air conduit including a housing having an upper and a lower port. The conduit coupling assembly may also include a recess disposed within the housing to receive secretions from the separate expiratory pathway, and may include an unidirectional valve disposed within the housing to direct the flow of gasses within said air conduit. In addition, the air conduit may have an internal partition positioned along its length that defines the inspiratory pathway and the separate expiratory pathway. The internal partition may be a flexible partition or a rigid partition.

In another general aspect, the present invention contemplates an endotracheal tube flow assembly for use with an endotracheal tube positionable within a patient, including a conduit coupling assembly having a housing with an upper and a lower port and a conduit connector coupled to the housing; and an expansible conduit coupled to the conduit connector positionable within an endotracheal tube in a co-axial relation. It is also contemplated that the expansible conduit include a wire or plastic stay to provide longitudinal support.

In a further embodiment, the present invention contemplates the conduit coupling assembly further including a recess disposed within the housing to receive secretions; a unidirectional valve disposed within said housing to direct the flow of gasses; an upper conduit connector coupled to the housing; and a lower conduit connector coupled to said housing. It is also contemplated that the housing include an access port communicating with the recess.

In a still further embodiment, the present invention includes an endotracheal tube coupled to the lower conduit connector such that the expansible conduit is positioned within the endotracheal tube.

In a further aspect, the present invention comprises a combination flow director and trap assembly for use with an endotracheal tube. The assembly includes a housing with an upper flow connector and a lower flow connector; a fluid trap or collector at its lower end; an expansible tube extending from the housing down through the flow connector; and an annular, valved partition defining an annular chamber within the housing below the partition. The lower flow connector is adapted to be connected to the upper or proximal end of the endotracheal tube so as to form an annular passageway between the endotracheal tube and the expansible tube. The upper flow connector is adapted to receive air or other desired gas from a suitable source. The partition includes a one-way flow valve or other device for enabling flow of gas selectively up through the housing.

In another form, the housing further includes a tube extending down through the upper flow connector and connecting at its lower end with the upper end of the expansible tube so as to enable air or other desired gas to flow from a suitable source to the expansible tube. The upper flow connector may then serve as a vent for the flow of gases passing through the one-way valve.

In a further aspect, the present invention provides a novel method for improving the removal of internal secretions from intubated patients. Inspiratory gasses are directed through the middle of the expansible tube, while expiratory gasses are directed between the walls of the endotracheal tube and the expansible tube. Each successive discharge of expiratory gasses moves internal secretions within the patient further up the sides of the endotracheal tube. Secretions collect in a receptacle at the proximal end of the endotracheal tube. The collected secretions may then be removed from the receptacle through standard suctioning techniques or collected by an absorbent material, without the need for direct suctioning of secretions from within the patient at the distal end of the endotracheal tube.

In a further broad respect, the present invention contemplates a method for removing secretions from lungs of an intubated patient including intubating a patient with an air conduit having an inspiratory pathway and a separate expiratory pathway; circulating a gas down said inspiratory pathway and up said separate expiratory pathway under flow conditions sufficient to move liquid within said patient's lungs during exhalation, if said liquid is present, up said separate expiratory pathway; and separating said liquid from said circulated gas at the upper end of said separate expiratory pathway.

In a more detailed respect, the invention contemplates a method for removing secretions from lungs of an intubated patient, including the steps of intubating a patient with a first conduit; supporting an expansible conduit within the first conduit to define an annular passageway within the first conduit; circulating a gas down the expansible conduit and up the annular passageway under flow conditions sufficient to expand the expansible conduit during inhalation and to move liquid within the patient's lungs during exhalation, if the liquid is present, up the annular passageway; and separating the liquid from said circulated gas at the upper end of the annular passageway. In a further embodiment, the method includes the step of sealing off any annular passageway existing between the first conduit and the patient's trachea.

Advantages and features of the present invention, may be better understood by reference to the following description and appended drawings, which form a part of this specification.

BRIEF DESCRIPTION OF THE DRAWINGS

It is to be noted, however, that the appended drawings illustrate only particular embodiments of the invention and are, therefore, not to be considered limiting of its scope, for the invention may admit to other effective embodiments.

DETAILED DESCRIPTION

The present invention contemplates a method and apparatus for directing air flow within an intubated patient to reduce or eliminate the need for direct suctioning of secretions from within the patient. To allow this capability, the present invention provides an air conduit with separate pathways for inspiratory and expiratory gasses. By so doing, each exhalation by the patient forces secretions within the lungs of the patient up and out of the patient, so that they may be collected and removed without the need for direct suctioning at the distal end of the tube that is within the intubated patient. Because the inhalation gasses pass through a separate pathway, they do not force secretions back down into the patient's lung.

Figure 1:
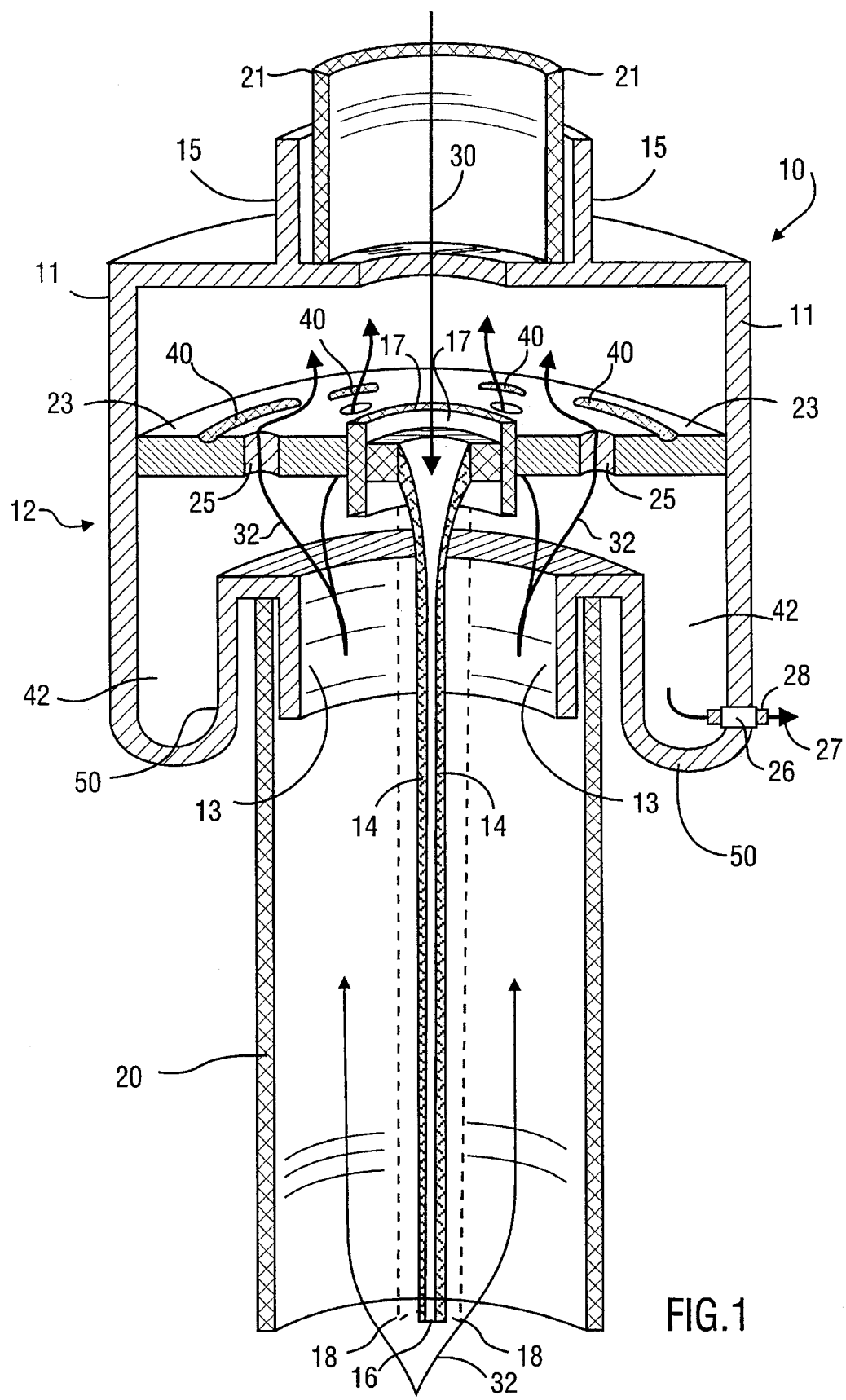
FIG. 1 is diagram of an endotracheal tube flow assembly according to the present invention.

FIG. 1 is one embodiment of an endotracheal tube flow assembly 10 according to the present invention, which includes a conduit coupling assembly 12 and an expansible conduit 14. Expansible conduit 14 may have a natural closed position 16. Expansible conduit 14 may be inflated, for example to expanded position 18, and may be adapted to substantially fill an endotracheal tube. The proximal end of expansible conduit 14 is secured to an internal conduit coupling 17 disposed within conduit coupling assembly 12, such that expansible conduit 14 may be suspended within an endotracheal tube 20. Internal conduit connector 17 may be supported within conduit coupling assembly 12 by struts, spokes, or partition 23.

Housing 11 of conduit coupling assembly 12 also includes a lower conduit connector 13 to interface with endotracheal tube 20 and an upper conduit connector 15 to interface with an externally extending conduit, such as may be connected to tubing 21 leading to a source of air, oxygen or other desired gas or mixture of gases. The lower end of conduit coupling assembly 12 is shaped to define an annular channel or recess 42 capable of serving as a collecting basin or receptacle for liquids and particles expelled from the patient's lungs.

Conduit coupling assembly 12 also includes unidirectional air flow valve 40 disposed above partition 23. Unidirectional air flow valve 40 allows exhalation gasses 32 to pass through port 25 but forces inhalation gasses 30 to travel through expansible conduit 14. It must be noted that a variety unidirectional valves may be used in the present invention for unidirectional flow valve 40.

Figure 2:
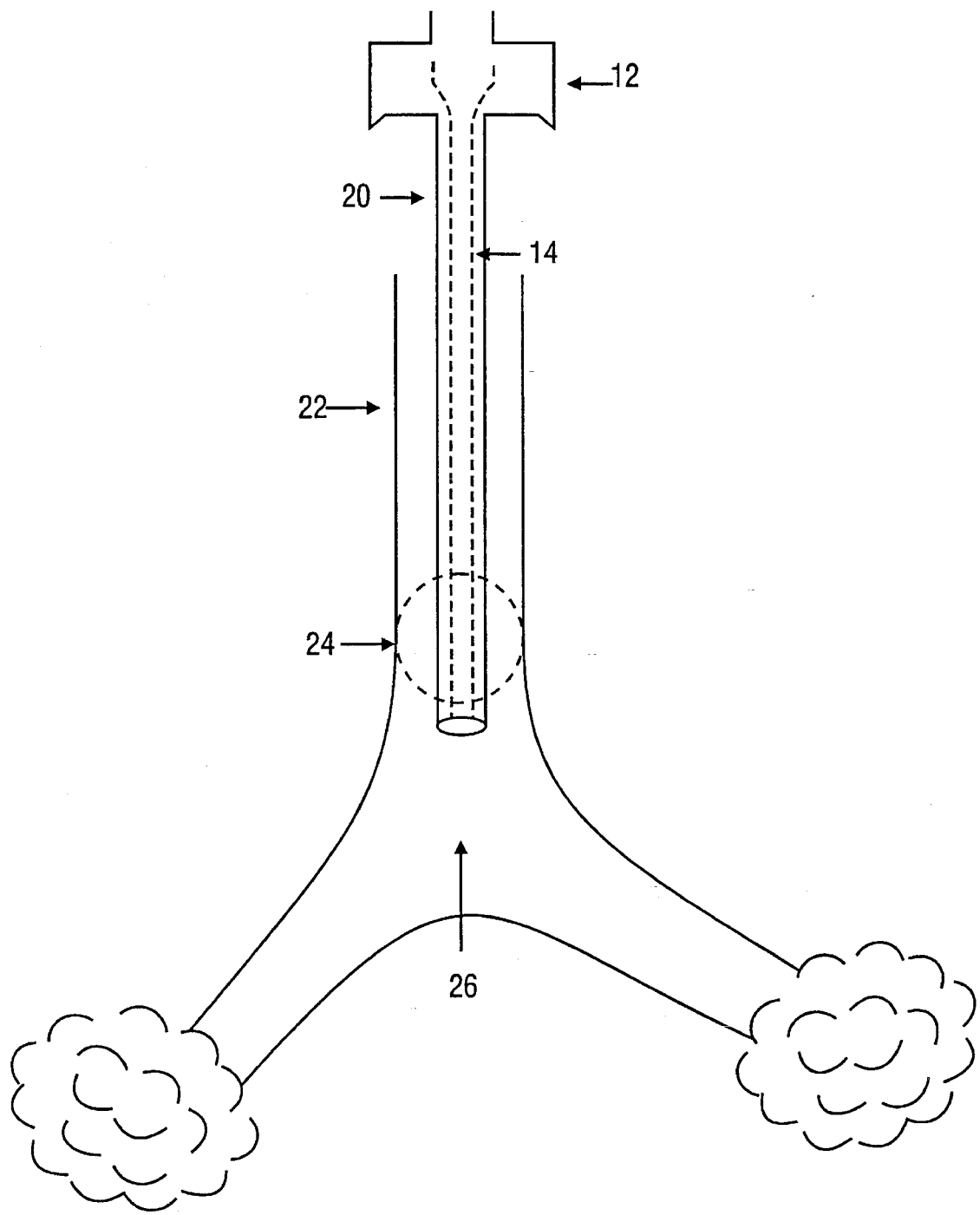
FIG. 2 is a diagram of an endotracheal tube flow assembly within an endotracheal tube located within a patient's trachea.

FIG. 2 is a schematic diagram of endotracheal tube flow assembly 10 according to the present invention coupled to an endotracheal tube 20 positioned within a trachea 22. Endotracheal tube 20 has an inflatable cuff 24. Inflatable cuff 24 may be inflated to seal trachea 22 except for air flow through endotracheal tube 20.

Expansible conduit 14 may be made of any material which will remain closed upon the pressure of exhalation gasses 32, and will expand upon the pressure of inhalation gasses 30. For example, expansible conduit 14 may be a section of flat latex tubing cut to be substantially the same length as endotracheal tube 20 (e.g., 18 inches). The diameter of expansible conduit 14 may be adjusted depending upon the diameter of endotracheal tube 20. Longitudinal stiffness may be given to the expansible conduit 14 by use of a wire or plastic stay. For example, stainless steel wires may be encapsulated by the latex along the longitudinal length of the latex tubing during the dipping process in which the latex tubing is created. In addition, baffles may be attached to the outside of expansible conduit 14 to augment movement of secretions.

Endotracheal tube 20 may be any standard endotracheal tube. For example, endotracheal tube 20 may be a standard endotracheal tube that has a standard endotracheal tube connector at its proximal end and that may be obtained from Sheridan Catheter Corporation or Mallinckrodt Medical, Inc. As contemplated by the present invention, endotracheal tube 20 may also take the form of other air conduits inserted into a patient's trachea or lungs, such as a tracheostomy tube. An endotracheal tube embodiment is described because they are commonly used in intubating patient's.

Conduit coupling assembly 12 may be of a variety of structures, including polyvinylchloride (PVC) fittings that may be purchased from a hardware store. Lower conduit connector 13 is designed to connect to the standard connector at the proximal end of a standard endotracheal tube. Annular channel or recess 42 may be a simple groove within housing 11. Alternatively, wall 50 of recess 42 may be angled to create a v-shaped cross-section that forces secretions toward the outside edge of recess 42. Other configurations for recess 42 may be used so long as recess 42 is capable of holding secretions.

To provide for removal of secretions, housing 11 may also include an access port 26 to which a suctioning device may be connected to suction secretions from recess 42 along path 27. Further, a stopper 28 may be provided to plug port 26 to allow secretions to pool. Alternatively, recess 42 may be filled with an absorbent material that may be removed at periodic intervals. As a further alternative, a permanent suctioning tube or device may be connected to recess 42 in fluid communication with secretions pooling in recess 42.

Figure 3:
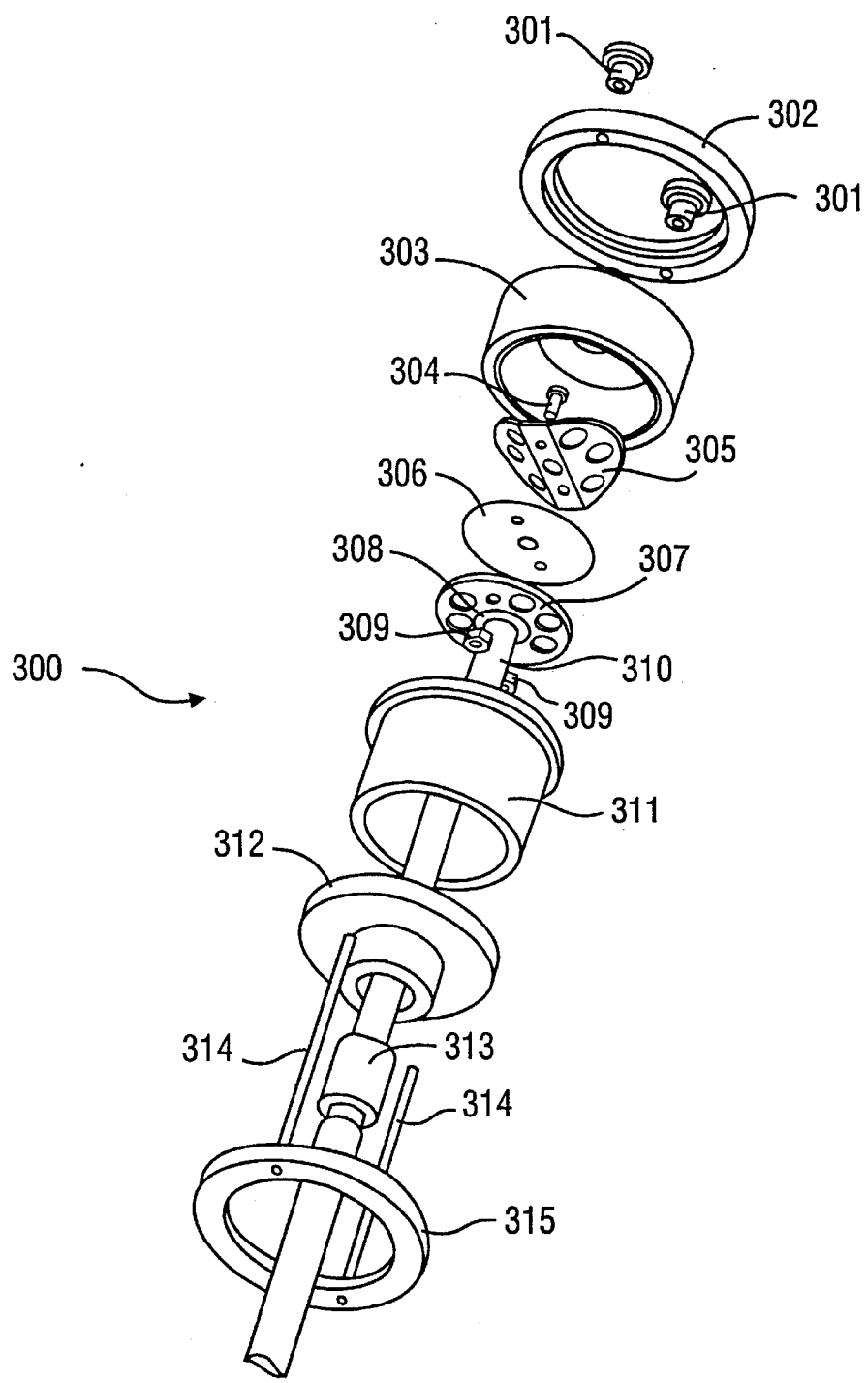
FIG. 3 is a diagram of an alternative embodiment of an endotracheal tube flow assembly according to the present invention.
Figure 4:
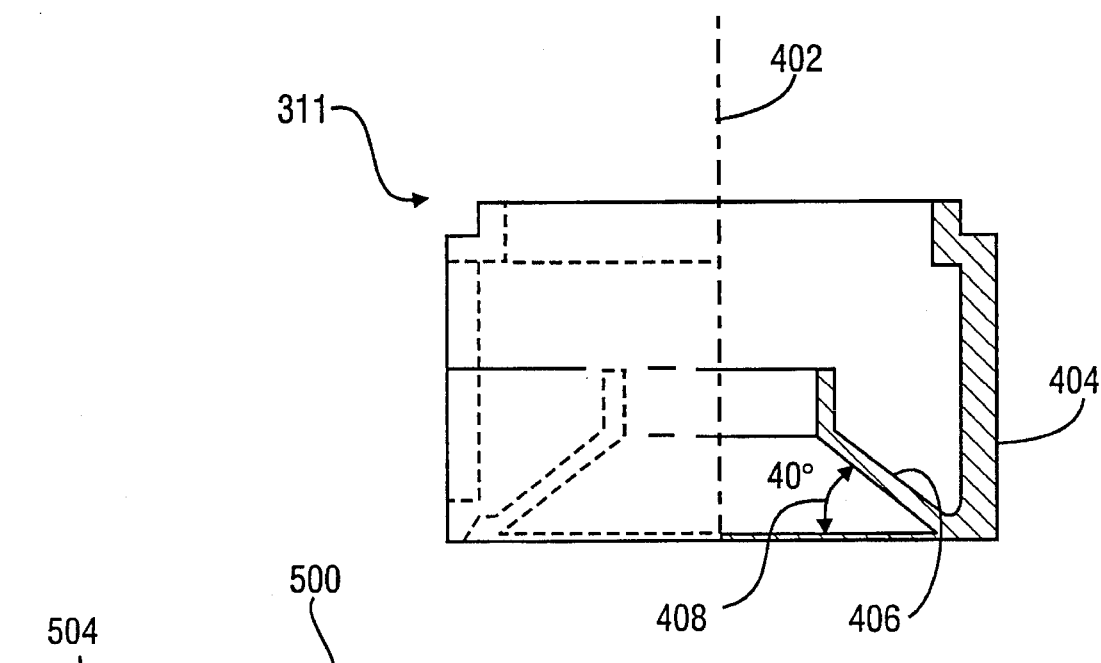
FIG. 4 is a cross-sectional diagram of a v-shaped reservoir for an alternative embodiment of an endotracheal tube flow assembly according to the present invention.

FIG. 3 is a schematic drawing of an alternative embodiment of an endotracheal tube flow assembly according to the present invention. Endotracheal flow assembly 300 includes bottom end ring 3 15, output cap 312, valve body 311, input cap 303, and top end ring 302. Valve body 311, as shown in FIG. 4, may have a v-shaped recess formed by the intersection of walls 404 and 406. Center line 402 represents the axial center of device 300. The exterior angle 408 formed by walls 404 and 406 may be of various angles, for example, 40° as in the embodiment shown in FIG. 4. Bottom end ring 315 and top end ring 302 have an annular flange in which input cap 303 and output cap 312 rest. Threaded rods 314 are fixed within bottom end ring 315, extend through top end ring 302, and are held by knurled thumb nuts 301. The valve assembly includes primary plate 307, flapper valve 306, and secondary plate 305, which are held together by binding heads 304 and hex nuts 309. Latex tube 310 is coupled to primary plate 307 through O-ring 308. Latex tube 310 extends through endotracheal tube 313 and may include two stainless steel wires embedded along its longitudinal length on opposite sides of latex tube 310.

The parts in endotracheal flow assembly 300 may be made from the following materials:

| | |
|---|---|
| bottom end ring 315 | 6061 aluminum |
| threaded rods 314 | stainless steel |
| endotracheal tube 313 | standard material |
| output cap 312 | white delrin |
| valve body 311 | lexan |
| latex tube 310 | latex |
| hex nuts 309 | stainless steel |
| O-ring 308 | rubber |
| primary plate 307 | 6061 aluminum |
| flapper valve 306 | latex |
| secondary plate 305 | 316 stainless steel |
| binding heads 304 | stainless steel |
| input cap 303 | lexan |
| top end ring 302 | 6061 aluminum |
| knurled thumb nuts 301 | stainless steel |

It should be noted that these materials are selected for a particular embodiment. Modifications to the selection of these materials may be made without parting from the present invention.

Looking to FIG. 1, in operation, inhalation gasses 30 are circulated within expansible conduit 14, forcing expansible conduit 14 into an expanded, open position 18. Exhalation gasses 32 are circulated outside of expansible conduit 14 but within endotracheal tube 20. During exhalation, expansible conduit 14 is in natural closed position 16. Unidirectional flow valve 40 acts to force inhalation gasses 30 through expansible conduit 14.

Exhalation gasses 32 flow through unidirectional valve 40 and out through the proximal end of conduit coupling assembly 12. Exhalation gasses 32 force internal secretions within a patient up the interior wall of endotracheal tube 20 and into conduit coupling assembly 12. The secretions collect within annular channel or recess 42. Because inhalation gasses 30 flow within expansible conduit 14, secretions are not forced back down into the patient's lungs. Without endotracheal tube flow assembly 10, which provides separate paths for inhalation gasses 30 and exhalation gasses 32, internal secretions would pool within a patient at the base of the tracheobronchial tree 26.

Experimentation with an endotracheal tube flow assembly, according to the present invention, has shown that secretions tend to be forced up the walls of endotracheal tube 20 by each successive burst of exhalation gasses 32. The present invention, therefore, allows expelled secretions to be collected and removed without having to contaminate the endotracheal tube system within the patient. Further, such collected secretions may be continuously removed, if so desired.

Figure 5A:
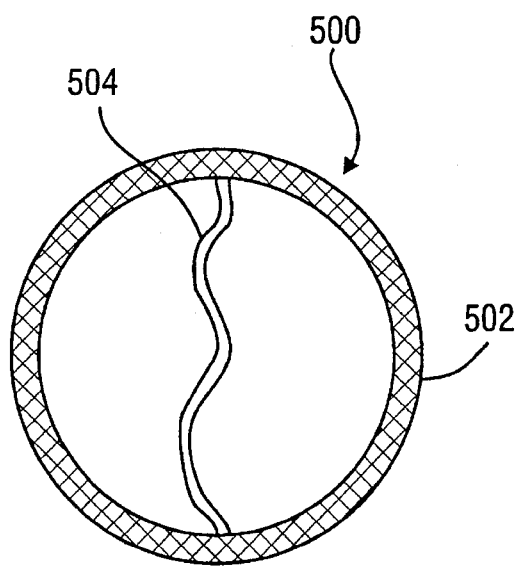
FIG. 5A is a cross-sectional diagram of an alternative embodiment of an endotracheal tube flow assembly according to the present invention having a flexible interior partition.
Figure 5B:
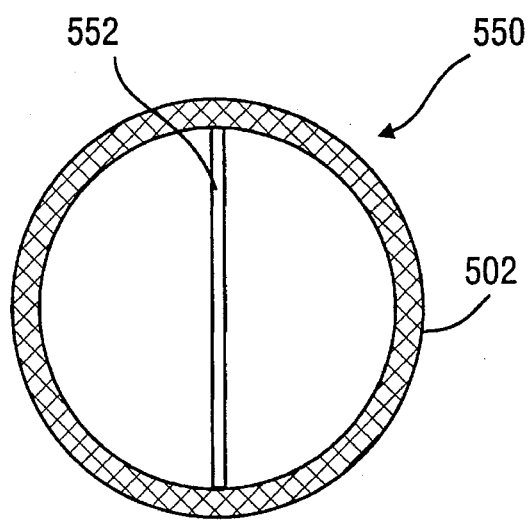
FIG. 5B is a cross-sectional diagram of an alternative embodiment of an endotracheal tube flow assembly according to the present invention having a rigid interior partition.

As mentioned above, the present invention, in broad respects, contemplates directing the air flow within an intubated patient to provide separate pathways for inspiratory and expiratory gasses. Thus, modifications to the above described structures are possible without parting from the present invention. FIG. 5A and FIG. 5B are two examples of such modifications. Alternative embodiment 500 shown in FIG. 5A provides separate inspiratory and expiratory pathways by inserting a flexible partition 504 into endotracheal tube 502. Alternative embodiment 550 shown in FIG. 5B provides separate inspiratory and expiratory pathways by inserting a rigid partition 552 into endotracheal tube 502. Both flexible partition 504 and rigid partition 552 may be made integral with endotracheal tube 502, if desired. In contrast to the embodiments shown in FIGS. 1–4, these embodiments do not rely upon a collapsible tube to provide the separate pathways. The valve and reservoir assemblies described above would be equally applicable to these embodiments as well, although some modifications may be necessary.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. An air flow assembly positionable within a patient to facilitate removal of secretions from within the patient without aspiration, said assembly comprising:

an air conduit positionable within a patient, said air conduit having an inspiratory pathway and a separate expiratory pathway;

a conduit coupling assembly coupled to said air conduit including a housing having an upper and a lower port; and air flow control means disposed within said housing for directing inhalation gasses through said inspiratory pathway to expand said patient's lungs and for allowing exhalation gasses to pass through said separate expiratory pathway to force secretions out of said patient through said separate expiratory pathway without aspiration by the force of exhalation gasses expulsed by a patient's lungs.

2. The air flow assembly of claim 1, Wherein said conduit coupling assembly further comprises a recess disposed within said housing to receive secretions from said separate expiratory pathway.

3. The air flow assembly of claim 2, wherein said air flow control means is an unidirectional valve disposed within said housing to direct the flow of gasses within said air conduit.

4. The air flow assembly of claim 2, wherein said air conduit is an endotracheal tube.

5. The air flow assembly of claim 1, wherein said air conduit has an internal partition positioned along its length, said partition defining said inspiratory pathway and said separate expiratory pathway.

6. The air flow assembly of claim 5, wherein said internal partition is a flexible partition.

7. The air flow assembly of claim 5, wherein said internal partition is a rigid partition.

8. An air flow assembly for use with an air conduit that is positionable within a patient to facilitate removal of secretions from within the patient without aspiration, said assembly comprising:

a conduit coupling assembly comprising:
      a housing having an upper and a lower port, and
      a conduit connector coupled to said housing;

an expansible conduit secured to said conduit connector positionable within an air conduit in a co-axial relation, said expansible conduit having a closed rest position: and air flow control means disposed within said housing for directing inhalation gasses inside said expansible conduit to provide an inspiratory pathway and for allowing exhalation gasses to pass outside of said expansible conduit to provide a separate expiratory pathway and to force secretions out of said patient through said separate expiratory pathway without aspiration by the force of exhalation gasses expulsed by a patient's lungs.

9. The air flow assembly of claim 8, wherein said expansible conduit is latex tubing.

10. The air flow assembly of claim 8, wherein said expansible conduit includes at least one longitudinal support.

11. The air flow assembly of claim 8, wherein said conduit coupling assembly further comprises a recess disposed within said housing to receive secretions.

12. The air flow assembly of claim 11, wherein said housing includes an access port communicating with said recess.

13. The air flow assembly of claim 11, wherein said air flow control means is an unidirectional valve disposed within said housing to direct the flow of gasses.

14. The air flow assembly of claim 13, wherein said conduit coupling assembly further comprises an upper conduit connector and a lower conduit connector.

15. The air flow assembly of claim 13, further comprising an endotracheal tube coupled to said lower conduit connector, said expansible conduit being positioned within said endotracheal tube.

16. A method for removing secretions from lungs of an intubated patient without aspiration, comprising:

intubating a patient with a first conduit;

supporting an expansible conduit having a closed rest position within said first conduit to define an annular passageway within said first conduit;

directing a gas down said expansible conduit under flow conditions sufficient to expand said expansible conduit during inhalation and to expand said patient's lungs;

stopping said gas from flowing down through said expansible conduit;

allowing said patient's lungs to expulse exhalation gasses up said annular passageway to move liquid within said patient's lungs during exhalation, if said liquid is present, up said annular passageway; and separating said liquid from said circulated gas at the upper end of said annular passageway.

17. The method of claim 16, wherein said supporting step, comprises:

connecting said first conduit to a lower conduit connector of a conduit coupling assembly;

connecting said expansible conduit to said conduit coupling; and positioning an unidirectional valve within said housing to direct the flow of gasses within said expansible conduit.

18. The method of claim 16, further comprising:

sealing off any annular passageway existing between said first conduit and said patient's trachea.

19. The method of claim 18, wherein said intubating step comprises intubating a patient with an endotracheal tube as the first conduit.

20. A method for removing secretions from lungs of an intubated patient without aspiration, comprising:

intubating a patient with an air conduit having an inspiratory pathway and a separate expiratory pathway;

directing a gas down said inspiratory pathway under flow conditions sufficient to expand said patient's lungs during inhalation;

stopping said gas from flowing down through said inspiratory pathway;

allowing said patient's lungs to expulse exhalation gasses up said separate expiratory pathway to move liquid within said patient's lungs during exhalation, if said liquid is present, up said separate expiratory pathway; and separating said liquid from said circulated gas at the upper end of said separate expiratory pathway.

\* \* \* \* \*